(12) United States Patent
O'Rear

(10) Patent No.: US 8,324,413 B2
(45) Date of Patent: Dec. 4, 2012

(54) LOW MELTING POINT TRIGLYCERIDES FOR USE IN FUELS

(75) Inventor: Dennis J. O'Rear, Penngrove, CA (US)

(73) Assignee: Texaco Inc., San Ramon, CA (US)

( * ) Notice: Subject to any disclaimer, the term of this patent is extended or adjusted under 35 U.S.C. 154(b) by 288 days.

(21) Appl. No.: 12/639,714

(22) Filed: Dec. 16, 2009

(65) Prior Publication Data

US 2010/0263263 A1    Oct. 21, 2010

Related U.S. Application Data

(60) Provisional application No. 61/140,356, filed on Dec. 23, 2008.

(51) Int. Cl.
*C11C 3/00* (2006.01)

(52) U.S. Cl. .................................. 554/168; 554/169

(58) Field of Classification Search ................ 554/168, 554/169
See application file for complete search history.

(56) References Cited

U.S. PATENT DOCUMENTS

| | | |
|---|---|---|
| 4,436,889 A | 3/1984 | Gauthier-Lafaye et al. |
| 4,440,871 A | 4/1984 | Lok et al. |
| 4,518,798 A | 5/1985 | Kramer et al. |
| 4,568,663 A | 2/1986 | Mauldin |
| 4,990,007 A | 2/1991 | Schmidt et al. |
| 5,059,718 A | 10/1991 | Vargas et al. |
| 5,135,638 A | 8/1992 | Miller |
| 5,167,774 A | 12/1992 | Berg |
| 5,282,958 A | 2/1994 | Santilli et al. |
| 5,434,279 A | 7/1995 | Wimmer |
| 5,512,692 A | 4/1996 | Peter et al. |
| 6,183,894 B1 | 2/2001 | Adzic et al. |
| 6,362,367 B2 | 3/2002 | Braithwaite et al. |
| 6,762,319 B1 | 7/2004 | Fache et al. |
| 6,833,065 B2 | 12/2004 | O'Rear |
| 6,846,402 B2 | 1/2005 | Hemighaus et al. |
| 6,916,951 B2 | 7/2005 | Tustin et al. |
| 7,147,775 B2 | 12/2006 | Dancuart Kohler et al. |
| 7,150,831 B2 | 12/2006 | Dancuart Kohler et al. |
| 7,153,393 B2 | 12/2006 | Dancuart Kohler et al. |
| 7,153,432 B2 | 12/2006 | Kohler et al. |
| 7,166,219 B2 | 1/2007 | Kohler et al. |
| 2003/0167681 A1* | 9/2003 | Delgado Puche ............... 44/388 |
| 2008/0184616 A1 | 8/2008 | Manoranjan et al. |

FOREIGN PATENT DOCUMENTS

| | | |
|---|---|---|
| EP | 0509079 | 10/1992 |
| EP | 1580255 | 9/2005 |
| WO | 2008-007231 | 1/2008 |

OTHER PUBLICATIONS

International Search Report and Written Opinion, International Application No. PCT/US2009/068782, dated Aug. 9, 2010.

\* cited by examiner

*Primary Examiner* — Deborah D Carr
(74) *Attorney, Agent, or Firm* — Melissa Patangia; Parul Anderson

(57) ABSTRACT

In the present invention, a fuel composition and a process for making the same are disclosed. Specifically, in the present invention, triglycerides useful for distillate fuels are described along with their method for preparation from Fischer-Tropsch acid by-products and the glycerol by-product from biodiesel generation. By using these two by-product streams, the overall efficiency of both processes is improved and a new source of distillate fuels is created. These triglycerides can be used to improve the lubricity of Fischer-Tropsch derived distillate fuels. In addition, these triglycerides also have low melting points and have viscosities compatible with distillate fuels.

2 Claims, 3 Drawing Sheets

LOW MELTING POINT TRIGLYCERIDES FOR USE IN FUELS

CROSS-REFERENCE TO RELATED APPLICATIONS

Priority of U.S. Provisional Patent Application No. 61/140,356, filed Dec. 23, 2008, is claimed under 35 U.S.C. §119.

FIELD OF THE INVENTION

The present invention relates generally to a fuel composition and a process for making the same and specifically to low melting point triglycerides for use in fuels.

BACKGROUND OF THE INVENTION

Triglycerides from plants and animals, such as vegetable oil and animal fats, consist of long chains of acids which esterify glycerol. These triglycerides have melting points and viscosities that are too great to use in either diesel fuel or jet fuel in conventional engines.

The physical properties of various triglycerides and other oxygenates are summarized in the below table.

| Name | Formula | MW | CAS ID | Boiling Point, °C. | Melting Point, °C. | Density, g/cm3 | Viscosity, cSt at 40° C. |
|---|---|---|---|---|---|---|---|
| Methanol | $CH_3OH$ | 32 | 67-56-1 | 64 | −97.8 | 0.7914 | 0.58 |
| Glycereol | $C_3H_8O_3$ | 92 | 56-81-5 | 290(d) | 18.6 | 1.2613 | 310 |
| Acetic Acid | $C_2H_4O_2$ | 60 | 64-19-7 | 118 | 16.6 | 1.0491 | 1.16 |
| Propanoic Acid | $C_3H_6O_2$ | 74 | 79-09-4 | 141 | −20.8 | 0.992 | 0.85 |
| Butanoic Acid | $C_4H_8O_2$ | 88 | 107-92-6 | 163 | −6.8 | 1.3991 | 0.82 |
| Methyl Ethylanoate | $C_3H_6O_2$ | 74 | 79-20-9 | 57 | −98 | 0.8740 | |
| Methyl Propanoate | $C_4H_8O_2$ | 88 | 554-12-1 | 78.7 | −87.5 | 0.9151 | |
| Methyl Butanoate | $C_5H_{10}O_2$ | 102 | 623-42-7 | 102.6 | <−95 | 0.8984 | |
| Glycerol-triethylanoate | $C_9H_{14}O_6$ | 218 | 102-76-1 | 259 | +3.2 | 1.1562 | 7.02 |
| tripropanoate | $C_{12}H_{20}O_6$ | 260 | 139-45-7 | 282 | <−50 | 1.100 | |
| tributylanoate | $C_{15}H_{26}O_6$ | 302 | 60-01-5 | 308 | −75 | 1.0350 | 5.30 |
| tripentylanoate | $C_{18}H_{32}O_6$ | 344 | 620-68-8 | | | 1.023 | |
| trihexylanoate | $C_{21}H_{38}O_6$ | 386 | 621-70-5 | 386 | −60 | 0.8752 | 8.71 |
| triheptylanoate | $C_{24}H_{44}O_6$ | 428 | 620-67-7 | 470 | | 0.966 | |
| trioctylanoate | $C_{27}H_{50}O_6$ | 470 | 538-23-8 | | +8.3 | 0.95 | 11.57 |
| tridecylanoate | $C_{33}H_{62}O_6$ | 555 | 621-71-6 | | +32 | 0.92 | 20.1 |
| tridodecylanoate | $C_{39}H_{74}O_6$ | 635 | 538-24-9 | | +46 | 0.9 | 23.7 |
| Glycerol-monoethylanoate | $C_5H_{10}O_4$ | 134 | 26446-35-5 | | −99 | 1.2060 | |
| diethylanoate | $C_7H_{12}O_5$ | 176 | 105-70-4 | 260 | 40 | 1.184 | |
| dibutanoate | $C_{11}H_{20}O_5$ | 232 | 32648-01-4 | 273 | | 1.066 | |

As the data in the above table illustrates, the chain length of the triglycerides influences the physical properties of the triglycerides.

For comparison, while the specification properties for diesel fuel and jet fuel can vary between countries and with the season, the typical properties of diesel fuel and jet fuel are summarized in the below table.

| Name | TBP Boiling Range, °C. | Cloud Point, °C. | Freeze Point, °C. | Density, g/cm3 | Viscosity, cSt at 40° C. |
|---|---|---|---|---|---|
| Diesel Fuel | 145-370 | −10 to −25 | | 0.82 to 0.86 | 1.9 to 4.1 |
| Biodiesel | 165-180 | +2 to +14 | | 0.86 to 0.90 | 3.5 to 5.0 |
| Jet Fuel | 120-290 | | <−40 | 0.775 to 0.840 | 1.5 to 3.5 |
| Fischer Tropsch Diesel | 124-374 | −18 | | 0.768 | 1.981 |

Consequently, in current commercial practice, the long-chain triglycerides are converted to lower viscosity methyl esters by transesterification, typically with a mixture of methanol and a base such as sodium hydroxide. This methyl ester product is commonly called a biodiesel. In general, neat biodiesel (methyl esters) have unacceptably high cloud points and viscosities that are slightly higher than that commonly used in conventional diesel engines. Thus, biodiesel is typically used as a blend with lower cloud point petroleum diesel.

In comparison to the long-chain triglycerides from plants and animals, short-chain triglycerides and cold-climate mixed-chain triglycerides can be used as fuels or fuel blending components. Most short-chain triglycerides have viscosities closer to the values of diesel fuel, can be distilled, and have melting points compatible with diesel fuel.

Another problem with the current approach of making methyl esters, is the by-product glycerol. The transesterification process creates glycerol which can be contaminated with the base used in the preparation of the methyl ester. Glycerol is a highly viscous liquid due to its three hydroxyl groups which interact between molecules via hydrogen bonding. Glycerol is too viscous to be used as diesel fuel. In addition, glycerol has a high melting point and decomposes during distillation. Glycerol has a limited market in some products like explosives (nitroglycerine), cosmetics, and lubricants. The volume of glycerol that will be produced as biofuels grow in production will be in great excess of these limited markets. The yield of glycerol by-product is about ten weight percent of the biodiesel product. Research programs have been launched to find uses for the glycerol by-product. It is desirable to find a way to use the glycerol by-product as a fuel or as a blending component in a fuel.

When glycerol is only partially esterified to form mono- and di-glycerides, the product is still too viscous due to the hydrogen bonding of the remaining hydroxyl groups. While measured viscosities at 40° C. for these compounds have not been reported, they are known to be viscous liquids. The mono- and di-esters of glycerol are known to form emulsions, a property which is generally not desirable in diesel fuel and jet fuels as this makes the separation of water from the fuels difficult.

Another way to convert biomass into a biofuel is to gasify the biomass to make synthesis gas (commonly referred to as "syngas"). The syngas can then be reacted over a Fischer-Tropsch process to make a mixture of compounds that can be converted into fuels by a combination of processes including, but not limited to, the following: hydrocracking, hydroisomerization, polymerization, and combinations thereof. Because of their high content of parafins, fuels derived from a Fischer-Tropsch process are known to have problems with poor lubricity, low density, and low viscosity.

In addition, the Fischer-Tropsch process makes an equivalent mass of water by-product for the mass of the hydrocarbon product. The water by-product is often contaminated with oxygenates such as alcohols and acids. It is known that the alcohols can be separated from the acid and water. The acid water mixture is typically purified by biological oxidation wherein the acids are consumed by microorganisms. This represents both a loss in product and an inefficiency in the process.

For these reasons, a way to convert glycerol into a useful fuel product; a way to improve the yield of fuel products from biomass synthesis; a way to reduce the loss in products from a Fischer-Tropsch process; and a way to improve the density, viscosity, and lubricity of Fischer-Tropsch fuels is needed.

SUMMARY OF THE INVENTION

In the present invention, a fuel composition and a process for making the same are disclosed. In one embodiment of the present invention, low melting point triglycerides useful for distillate fuels are described along with their method for preparation from Fischer-Tropsch acid by-products and the glycerol by-product from biodiesel generation. By using these two by-product streams, the overall efficiency of both processes is improved and a new source of distillate fuels is created. These triglycerides can be used to improve the lubricity of Fischer-Tropsch derived distillate fuels. In another embodiment of the present invention, low melting point triglycerides are described along with their method of preparation by transesterifying natural triglycerides with short chain esters. The fuel composition of the present invention has both a low melting point and viscosities compatible with distillate fuels.

BRIEF DESCRIPTION OF THE FIGURES

The description is presented with reference to the accompanying figures in which.

Figure 1:
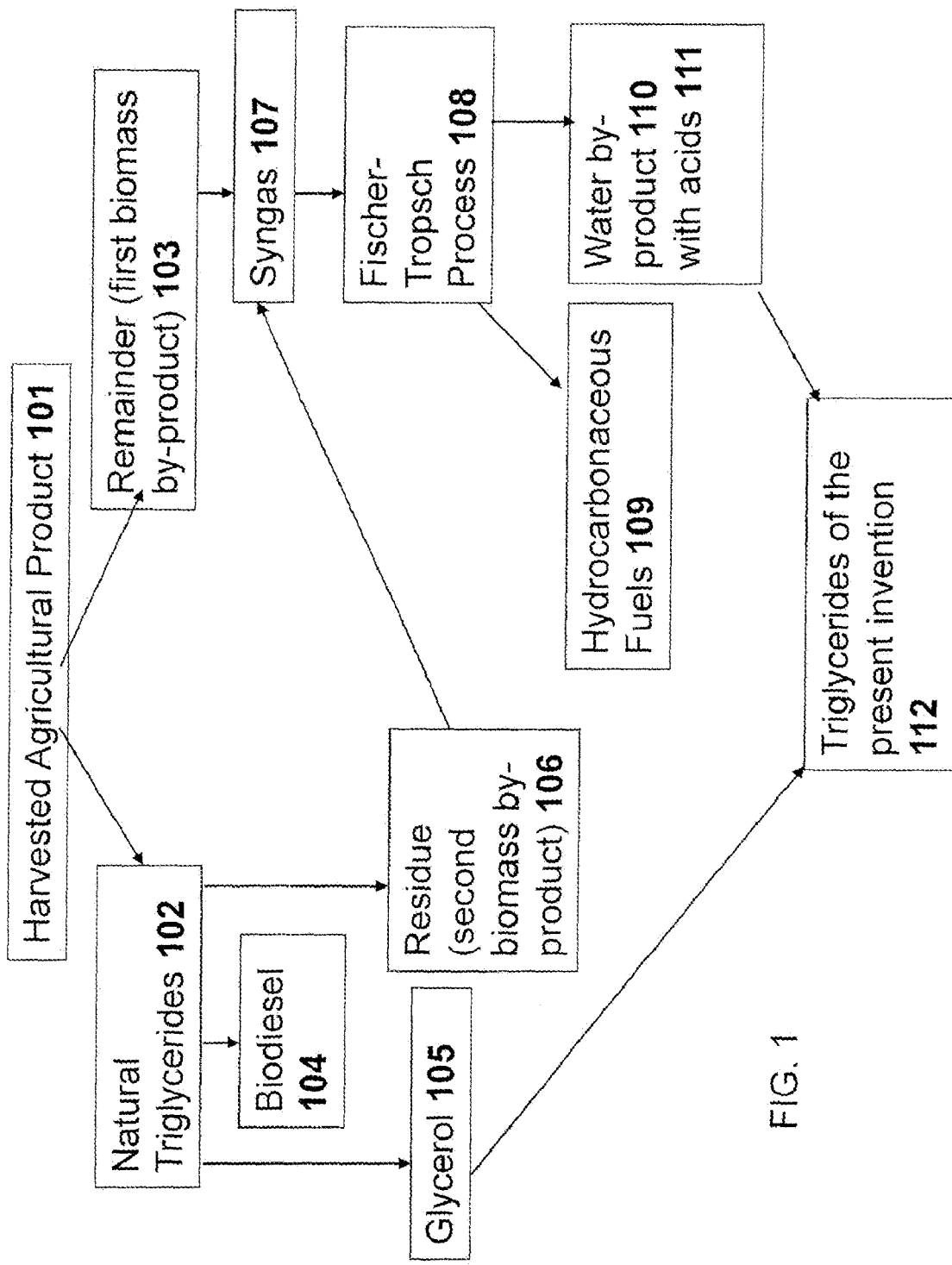
FIG. 1 depicts a process flow diagram of one embodiment of the process for making a fuel composition of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

In the present invention, triglycerides useful for distillate fuels are disclosed along with their method for preparation from Fischer-Tropsch acid by-products and the glycerol by-product from biodiesel generation. The triglycerides of the present invention have a low melting point and a slightly high viscosity making them compatible with distillate fuels.

The triglycerides of the present invention may be added to a Fischer-Tropsch derived fuel, a petroleum derived fuel, a biodiesel, additives, or combinations thereof. The slightly high viscosity and high density of the triglycerides of the present invention can be used to improve the low viscosity and low density of Fischer-Tropsch derived fuels. In addition, the triglycerides of the present invention are oxygenates and are expected to also improve the lubricity of Fischer-Tropsch derived fuels.

1. Definitions

Certain terms are defined throughout this description as they are first used, while certain other terms used in this description are defined below:

"Biodiesel," as defined herein, is a non-petroleum-based diesel fuel with a renewable source of biological origin.

"Biofuel," as defined herein, is a fuel product at least partly derived from "biomass."

"Biomass," as defined herein, is a renewable resource of biological origin including, but not limited to, switchgrass, agricultural wastes, and forest residue.

"Fischer-Tropsch," as defined herein, refers to the Fischer-Tropsch synthesis process wherein liquid and gaseous hydrocarbons are formed by contacting a synthesis gas (syngas) comprising a mixture of $H_2$ and CO with a Fischer-Tropsch catalyst under suitable temperature and pressure reactive conditions. The products from the Fischer-Tropsch process may range from $C_1$ to $C_{200+}$ with a majority in the $C_5$ to $C_{100+}$ range. For examples of Fischer-Tropsch processes, see U.S. Pat. No. 7,179,311 and European Patent No. 0609079.

The Fischer-Tropsch reaction is typically conducted at temperatures from about 300 to 700° F. (149 to 371° C.); pressures from about 10 to 600 psia (0.7 to 41 bars); and catalyst space velocities from about 100 to 10,000 cc/g/hr.

The Fischer-Tropsch reaction can be conducted in a variety of reactor types including, but not limited to, fixed bed reactors containing one or more catalyst beds; slurry reactors; fluidized bed reactors; or a combination of these different types of reactors. Such reaction processes and reactors are well known and documented in the art. Slurry Fischer-Tropsch processes utilize superior heat (and mass) transfer characteristics for the strongly exothermic synthesis reaction and are able to produce relatively high molecular weight, paraffinic hydrocarbons when using a cobalt catalyst. In a slurry process, a syngas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions.

Suitable Fischer-Tropsch catalysts comprise one or more Group VIII catalytic metals such as Fe, Ni, Co, Ru, and Re. Additionally, a suitable catalyst may contain a promoter. An example of a Fischer-Tropsch catalyst comprises effective amounts of cobalt and one or more of Re, Ru, Pt, Ni, Th, Zr, Hf, U, Mg, and La on a suitable inorganic support material such as one which comprises one or more refractory metal oxides such as titania. The catalysts can also contain basic oxide promoters such as $ThO_2$, $La_2O_3$, MgO, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re. Support materials including alumina, silica, magnesia, and titania or mixtures thereof may be used. For examples of Fischer-Tropsch processes, see U.S. Pat. No. 4,568,663.

The products from Fischer-Tropsch reactions performed in slurry bed reactors generally include a light reaction product and a waxy reaction product. The light reaction product (i.e. the condensate fraction) includes hydrocarbons boiling below about 700° F. (e.g., tail gases through middle distillate), largely in the $C_5$ to $C_{20}$ range, with decreasing amounts up to about $C_{30}$. The waxy reaction product (i.e. the wax fraction) includes hydrocarbons boiling above about 600° F. (e.g., vacuum gas oil through heavy parrafins), largely in the $C_{20+}$ range, with decreasing amounts down to $C_{10}$. Both the light reaction product and the waxy product are substantially paraffinic. The waxy product generally comprises greater than 70% normal paraffins, and often greater than 80% normal paraffins. The light reaction product comprises paraffinic products with a significant proportion of alcohols and olefins. In some cases, the light reaction product may comprise as much as 50% and even higher alcohols and olefins.

The Fischer-Tropsch process can be divided into two types of processes—a low temperature process and a high temperature process. The low temperature Fischer-Tropsch process, which is generally carried out below 250° C., usually will produce high molecular weight products with low to moderate branching. The high temperature Fischer-Tropsch process, which is generally carried out at temperatures about 250° C., will produce lower molecular weight olefinic products generally within the $C_3$ to $C_8$ range. The olefinic products from the high temperature Fischer-Tropsch process usually undergo oligomerization and hydrogenation steps which produce a highly branched iso-paraffinic product having a branching index of 4 or greater. For examples of Fischer-Tropsch processes, see U.S. Pat. No. 6,846,402.

"Glycerol," as defined herein, is also known as glycerin or glycerine with the following formula: $C_3H_8O_3$. Glycerol is found in nature in the form of its esters, which are known as glycerides.

"Hydrocarbonaceous," as defined herein, generally refers to a gas, liquid, or solid material (hydrocarbonaceous material) that contains hydrogen and carbon and optionally oxygen, sulfur, nitrogen, or combinations of these elements. Hydrocarbonaceous fuels are hydrocarbanaceous materials that can be used as a jet fuel, diesel fuel, or combinations. Products from a Fischer-Tropsch process include hydrocarbonaceous materials that contain a mixture of paraffins, olefins, alcohols, and acids.

"Hydroprocessing," as defined herein, generally refers to reactions in the presence of a catalyst and hydrogen at high temperature and pressure for modification of hydrocarbonaceous material by saturation, isomerization, heteroatom removal, cracking, and the like. Hydrocracking and hydrotreating are examples of hydroprocessing reactions.

Hydrocracking is a process of breaking longer carbon chain molecules into smaller ones. It may be effected by contacting the particular fraction or combination of fractions, with hydrogen in the presence of a suitable hydrocracking catalyst at temperatures in the range of about from 600 to 900° F. (316 to 482° C.) and pressures in the range of from about 200 to 4000 psia (13-272 atm) using space velocities based on the hydrocarbon feedstock of about 0.1 to 10 $hr^{-1}$. Generally, hydrocracking is utilized to reduce the size of the hydrocarbon molecules, hydrogenate olefin bonds, hydrogenate aromatics, and remove traces of heteroatoms. Suitable catalysts of hydrocracking operations are known in the art. Fischer-Tropsch raw product may be subjected to hydrocracking over a sulfided catalyst.

Hydroisomerization involves contacting a waxy hydrocarbon stream with a catalyst, which contains an acidic component, to convert the normal and slightly branched iso-paraffins in the waxy stream to other non-waxy species and thereby generate a lube base stock product with an acceptable pour point. The contacting of the waxy stream and catalyst may be carried out in the presence of hydrogen. Typical conditions under which the hydroisomerization process may be carried out include temperatures from about 200 to 400° C. and pressures from about 15 to 3000 psig. The liquid hourly space velocity during contacting is generally from about 0.1 to 20. The hydrogen to hydrocarbon ratio falls within a range from about 1.0 to about 50 moles $H_2$ per mole hydrocarbon. Hydroisomerization converts at least a portion of the waxy feed to non-waxy iso-paraffins by isomerization, while at the same time minimizing conversion by cracking. The degree of cracking is limited so that the yield of less valuable by-products boiling below the lube base oil range is reduced and the yield of lube base oil is increased. Hydroisomerization generates a lube base oil with higher VI and greater oxidation and thermal stability. In the hydroisomerization process, the waxy feed is contacted under isomerization conditions. For examples of hydroisomerization, see U.S. Pat. Nos. 4,440,871; 5,135,638; 5,282,958; and 6,833,065.

Hydrotreating is conducted using conventional hydrotreating conditions. Typical hydrotreating conditions vary over a wide range. In general, the overall liquid hourly space velocity (LHSV) is about 0.25 to 2.0. The hydrogen partial pressure is greater than 200 psia to about 2000 psia. Hydrogen recirculation rates are typically greater than 50 SCF/Bbl up to 5000 SCF/Bbl. Temperatures range from about 300° F. to about 750° F. Catalysts useful in hydrotreating operations are well known in the art and include noble metals from Group VIIIA such as platinum or palladium on an alumina or siliceous matrix, and unsulfied Group VIIIA and Group VIB such as nickel-molybdenum or nickel-tin on an alumina or siliceous matrix. The non-noble metal (such as nickel-molybdenum) hydrogenation metals are usually present in the final catalyst compositions as oxides, or possibly as sulfides when such components are readily formed from the particular metal involved. The matrix component may be of many types including some that have acidic catalytic activity. More than one catalyst type may be used in the reactor.

"Short-chain acids," as defined herein, are acids from one (formic) to six (hexanoic and isomers) carbon atoms. Short chain acids can be either saturated or unsaturated (containing olefinic bonds).

"Short-chain esters," as defined herein, are esters of methanol, ethanol, or 1-propanol with acid molecules having from 1 (formic acid) and six (hexanoic acid and isomers) carbon atoms. Example of short-chain esters include methylethylanoate (methyl acetate), ethylethylanoate (ethyl acetate), and methylpropylanoate. Short chain esters can either be composed of saturated acids or the acids can be unsaturated (containing olefinic bonds).

"Synthesis gas" or "syngas," as defined herein generally refers to a gas mixture comprising carbon monoxide (CO), hydrogen ($H_2$), and optionally water ($H_2O$) and carbon dioxide ($CO_2$). The sulfur content of syngas used in a Fischer-Tropsch process should be as low as possible since the catalysts for a Fischer-Tropsch process are poisoned by sulfur. Similarly, nitrogen compounds such as ammonia and cyanides should also be minimized. Syngas is typically produced by gasification in a gasifier. General oxidative routes from hydrocarbons to syngas are as follows:

$$C_nH_{(2n+2)} + (n/2)O_2 \rightarrow nCO + (n+1)H_2$$

"Triglycerides," as defined herein, are glycerides in which the glycerol is esterified with three fatty acids. Triglycerides are the components of both vegetable oils and animal fats.

"Cold-climate mixed-chain triglycerides," as defined herein, are tri-esters of glycerol with three acid molecules where the acid molecules have two or three different carbon numbers, and having a melting point of less than or equal to 0° C., for example −90° C. to 5° C., or −75° C. to −5° C., or −50° C. to −10° C. Examples of cold-climate mixed-chain triglycerides are glycerol diethylanoate where a third acid has between three and twenty carbon numbers, such as glycerol diethylanoate monooctylanoate. Cold-climate mixed-chain triglycerides have the following formula when there is no unsaturation:

$$C_3H_5-(CO_2)_3-(CH_2)_x-(CH_2)_y-(CH_2)_z-H_3$$

where the values of x, y, and z are not all the same (either only two are the same or none are the same). The values of x, y, and z are greater than or equal to 0 and up to 19, for example x=y=1 (ethylanoate) and z is between 2 (propanoate) and 7 (octoanoate). Isomers of this formula are within the scope of this definition. Isomers include branched acids and different substitution positions on the glycerol backbone. Cold-climate mixed-chain triglycerides may also be composed of unsaturated acids in which case the formula would contain fewer hydrogen atoms.

"Long-chain triglycerides" as defined herein, are tri-esters of glycerol with three acid molecules having the same or different number of carbon atoms from seven and larger such as 14 to 22. Example of long-chain triglycerides include natural triglycerides (such as those harvested from plants, algae, and animal fat). Long-chain triglycerides have the following formula when there is no unsaturation:

$$C_3H_5-(CO_2)_3-(CH_2)_x-(CH_2)_y-(CH_2)_z-H_3$$

where the values of x, y, and z can be the same or different. Values of x, y, and z are from 13 to 21. Isomers of this formula are within the scope of this definition. Isomers include branched acids and different substitution positions on the glycerol backbone. Long-chain triglycerides may also be composed of unsaturated acids in which case the formula would contain fewer hydrogen atoms. When there is unsaturation in the acid chains, the formula for the long-chain triglycerides is as follows:

$$C_3H_5-(CO_2)_3-(CH_2)_{x-2xu}-(CH_1)_{2xu}(CH_2)_{y-2yu}-(CH_1)_{2yu}-(CH_2)_{z-2zu}-(CH_1)_{2zu}-H_3$$

Where xu, yu and zu are the numbers of unsaturated bonds in the x, y and z carbon chains respectively. Xu, yu and zu vary from 0 (fully saturated) to 6 with the limit that $2xu \leq x$, $2yu \leq y$, and $2zu \leq z$.

"Mixed-chain triglycerides," as defined herein, are tri-esters of glycerol with three acid molecules where the acid molecules have either two or three different carbon numbers. Mixed-chain triglycerides have the following formula when there is no unsaturation:

$$C_3H_5-(CO_2)_3-(CH_2)_x-(CH_2)_y-(CH_2)_z-H_3$$

where the values of x, y, and z are not all the same (either only two are the same or none are the same). Isomers of this formula are within the scope of this definition. Isomers include branched acids and different substitution positions on the glycerol backbone. Mixed-chain triglycerides may also be composed of unsaturated acids in which case the formula would contain fewer hydrogen atoms. When there is unsaturation in the acid chains, the formula for the mixed-chain triglycerides is as follows:

$$C_3H_5-(CO_2)_3-(CH_2)_{x-2xu}-(CH_1)_{2xu}(CH_2)_{y-2yu}-(CH_1)_{2yu}-(CH_2)_{z-2zu}-(CH_1)_{2zu}-H_3$$

Where xu, yu and zu are the numbers of unsaturated bonds in the x, y and z carbon chains respectively. Xu, yu and zu vary from 0 (fully saturated) to 6 with the limit that $2xu \leq x$, $2yu \leq y$, and $2zu \leq z$. xu, yu, zu, x, y and z must all be whole positive numbers.

"Short-chain triglycerides," as defined herein, are tri-esters of glycerol with three acid molecules having the same number of carbon atoms from one (formic acid) to six (hexanoic acid and isomers). Short-chain triglycerides will have melting points less than or equal to 5° C., for example −90° C. to 5° C., or −75° C. to −5° C., or −50° C. to −10° C. Short-chain triglycerides have the following formula when there is no unsaturation:

$$C_3H_5-(CO_2)_3-(CH_2)_x-(CH_2)_y-(CH_2)_z-H_3$$

where x=y=z and the value of x is greater than or equal to 0 (formic) and up to 5 (hexanoic). Isomers of this formula are within the scope of this definition. Isomers include branched acids. Short-chain triglycerides may also be composed of unsaturated acids in which case the formula would contain fewer hydrogen atoms. When there is unsaturation in the acid chains, the formula for the short-chain triglycerides is as follows:

$$C_3H_5-(CO_2)_3-(CH_2)_{x-2xu}-(CH_1)_{2xu}(CH_2)_{y-2yu}-(CH_1)_{2yu}-(CH_2)_{z-2zu}-(CH_1)_{2zu}-H_3$$

Where xu, yu and zu are the numbers of unsaturated bonds in the x, y and z carbon chains respectively. Xu, yu and zu vary from 0 (fully saturated) to 6 with the limit that $2xu \leq x$, $2yu \leq y$, and $2zu \leq z$. xu, yu, zu, x, y and z must all be whole positive numbers.

"Upgrading," as defined herein, refers generally to the processes to make jet and diesel fuels or jet and diesel fuel blending components from the products from a Fischer-Tropsch process (raw Fischer-Tropsch products). The processes used to upgrade the raw Fischer-Tropsch products include, but are not limited to, the following: dimerization and oligomerization (of olefins), hydrotreating (of Fischer-Tropsch condensates, waxes, and products of dimerization and oligomerization), hydrocracking (of Fischer-Tropsch condensates and waxes), and hydroisomerization (of Fischer-Tropsch condensates and waxes).

2. The Embodiments of the Fuel Composition of the Present Invention

The low melting point triglycerides of the present invention are useful as a fuel or a fuel blending additive component for cold climates. The triglycerides of the present invention have the following formula when there is no unsaturation:

$$C_3H_5-(CO_2)_3-(CH_2)_x-(CH_2)_y-(CH_2)_z-H_3$$

where the values of x, y, and z are not all the same, and the values of x, y, and z are greater than or equal to 0 and up to 19. Low melting point triglycerides may also be composed of unsaturated acids in which case the formula would contain fewer hydrogen atoms. When there is unsaturation in the acid chains, the formula for the low melting point triglycerides is as follows:

$$C_3H_5-(CO_2)_3-(CH_2)_{x-2xu}-(CH_1)_{2xu}(CH_2)_{y-2yu}-(CH_1)_{2yu}-(CH_2)_{z-2zu}-(CH_1)_{2zu}-H_3$$

Where xu, yu and zu are the numbers of unsaturated bonds in the x, y and z carbon chains respectively. Xu, yu and zu vary from 0 (fully saturated) to 6 with the limit that $2xu \leq x$, $2yu \leq y$, and $2zu \leq z$. xu, yu, zu, x, y and z must all be whole positive numbers. In one embodiment, x=1, y=1, and z is between 2 and 19. Xu=0, yu=0, and zu is 0, 1, 2, or 3. In another embodiment, z is between 2 and 7 and zu is zero or between 2 and 3 and zu is zero. In addition, the low melting point triglycerides of the present invention comprise less than 10 wt % of a sum of mono- and di-glyceride impurities or between 0.1 and 10 wt %, between 1 and 7 wt %, or between 2 and 5 wt %. Further, the low melting point triglycerides of the present invention have a melting point between −90° C. and 0° C., or between −75° C. and −5° C., or between −50° C. and −10° C.

The fuel composition of the present invention contains the low melting point triglycerides of the present invention in amounts from 0.1 wt % to 50 wt %. For example, embodiments of the fuel composition of the present invention may range from an amount from 1 wt % to 25 wt %, or 2 wt % to 15 wt %. Low levels of short-chain triglycerides and cold-climate mixed-chain triglycerides will be effective for improving the lubricity of the fuel. Higher levels will be effective for improving the lubricity, viscosity, and density.

3. The Embodiments of the Process for Making the Fuel Composition of the Present Invention In the embodiments of the present invention, the short-chain triglycerides and cold-climate mixed-chain triglycerides can be made from glycerol (such as derived as a by-product from biodiesel manufacture) and short chain acids (such as derived from a Fischer-Tropsch process) by esterification. In addition, the fuel composition of the present invention can also be made by transesterifying natural triglycerides with short chain esters. The alcohol in the short chain ester can be derived from alcohols in the water by-product from a Fischer-Tropsch process or made by using a portion of the synthesis gas used as a feed in a Fischer-Tropsch process (for example synthesis gas can be used to make methanol).

One embodiment of the process for making the fuel composition of the present invention is depicted in FIG. 1. In FIG. 1, the biodiesel process used to make the glycerol can be coupled with the Fischer-Tropsch process. For example, an agricultural product (corn, oil seed, et cetera) can be harvested 101 and the portions rich in natural triglycerides 102 separated from the remainder of the plant material 103 (a first biomass by-product).

The natural triglycerides 102 can be separated and used to make biodiesel 104, glycerol 105, and residue 106 (a second biomass by-product). Two different reagents can be used to transesterify the natural triglyceride to form a biodiesel. For example, an alcohol such as methanol may be used or an ester such as a mixture of methyl acetate, higher methyl esters, and esters of $C_2+$ alcohols (such as ethanol) with an acid may be used.

The first bio-by-product 103, the second bio-by-product 106, or combinations thereof can be gasified to make synthesis gas 107. The synthesis gas 107 can be reacted in a Fischer-Tropsch process 108 to make hydrocarbonaceous materials that are upgraded to make hydrocarbonaceous fuels 109. A water by-product 110 is also created from the Fischer-Tropsch process that contains alcohols and acids 111.

The hydrocarbonaceous asset used for the Fischer-Tropsch and the source of the natural triglycerides can be the same or different. This embodiment is an example of their being the same. Specifically, the use of residue from the extraction of natural triglycerides 103 (plant parts, non-triglycerides, et cetera) as a feed source for a gasifier that makes synthesis gas for use in the Fischer-Tropsch process.

The acids from the Fischer-Tropsch process 111 can be recovered and used to make short-chain triglycerides and cold-climate mixed-chain triglycerides 112 by esterification with the glycerol 105 from the biodiesel generation.

In other embodiments of the process for making the fuel composition of the present invention, natural triglycerides can be transesterified. While the acids in natural triglycerides can be either saturated or unsaturated, the sources for acids used for transesterification are typically saturated. There are two processes to transesterify natural triglycerides. The first process involves a reaction with an alcohol (such as methanol) in the presence of a catalyst (such as sodium hydroxide). The second process involves a reaction with an ester (such as methyl acetate) in the presence of a catalyst. For examples of such processes, see U.S. Pat. Nos. 5,434,279 and 5,512,692.

In the first natural triglyceride process, there are four sources for the acid used to convert the glycerol by-product into a short-chain triglyceride or a mixed-chain triglyceride.

First, the acid may be recovered from the Fischer-Tropsch by-product water. Second, the acid may be made by oxidation of Fischer-Tropsch alcohols. Third, the acid may be made by the OXO process of Fischer-Tropsch olefins to form aldehydes followed by oxidation. Fourth, the acid may be made by carbonlyation of Fischer-Tropsch alcohols, olefins, and combinations.

Acetic and higher acids can be recovered from the water by-product of a Fischer-Tropsch process and the methanol can be made by methanol synthesis using a portion of the synthesis gas used in or as a by-product of the Fischer-Tropsch process. If the acids recovered from the Fischer-Tropsch process are not exclusively acetic acid, but contain higher acids, the methyl esters will be a mixture of methyl acetate and methyl esters of higher acids. When this mix of esters is used to transesterify the natural triglycerides, the resulting glycerol ester will contain a mixture of acid groups and will be a mixed-chain triglyceride such as a cold-climate mixed-chain triglyceride. For examples of such processes, see U.S. Pat. No. 5,167,774.

Acids can also be synthesized from the alcohols recovered from the Fischer-Tropsch process (either from the waste water or present in the hydrocarbon products from the Fischer-Tropsch reactor). For examples of such processes, see U.S. Pat. Nos. 4,990,007; 6,183,894; 6,362,367; and 6,762,319. These acids are typically saturated.

Acids of three or more carbon numbers can be synthesized from Fischer-Tropsch olefins by the OXO process which forms aldehydes. The aldehydes can then be oxidized to form acids. The carbon monoxide for the OXO synthesis can be obtained from a portion of the synthesis gas used in or as a by-product of the Fischer-Tropsch process. The oxygen used in the oxidation of the aldehydes to acids can be obtained from the oxygen prepared by air separation and used in the manufacture of the synthesis gas. For examples of such processes, see U.S. Pat. No. 5,059,718. These acids are typically saturated.

Acids can also be made from Fischer-Tropsch olefins and/or alcohols by a process known as carbonylation. In carbonylation the carbon number of the resulting acid is the one number higher than the starting alcohol. For examples of such processes, see U.S. Pat. Nos. 4,436,889; 4,518,798; and 6,916,951. These acids are typically saturated.

In the first natural triglyceride process, there are three sources of the alcohol used to transesterify the natural triglyceride.

First, the alcohol may be purchased alcohol such as methanol. Second, the alcohol may be methanol made from a portion of the synthesis gas used in or as a by-product from the Fischer-Tropsch process. Third, the alcohol may be $C_2+$ alcohols formed in the Fischer-Tropsch process and recovered either from the water or from the hydrocarbon phase of the product. For examples of such processes, see U.S. Pat. Nos. 7,147,775; 7,150,831; 7,153,393; 7,153,432; and 7,166,219.

In the second natural triglyceride process, when an ester is used to transesterify the natural triglyceride, a short-chain triglyceride or a mixed-chain triglyceride is produced as a product along with the ester biodiesel. The methyl acetate for this process can be manufactured by reacting methanol and acetic acid.

As the above demonstrates, the process of the present invention includes numerous variations to make the fuel composition of the present invention.

Figure 2A:
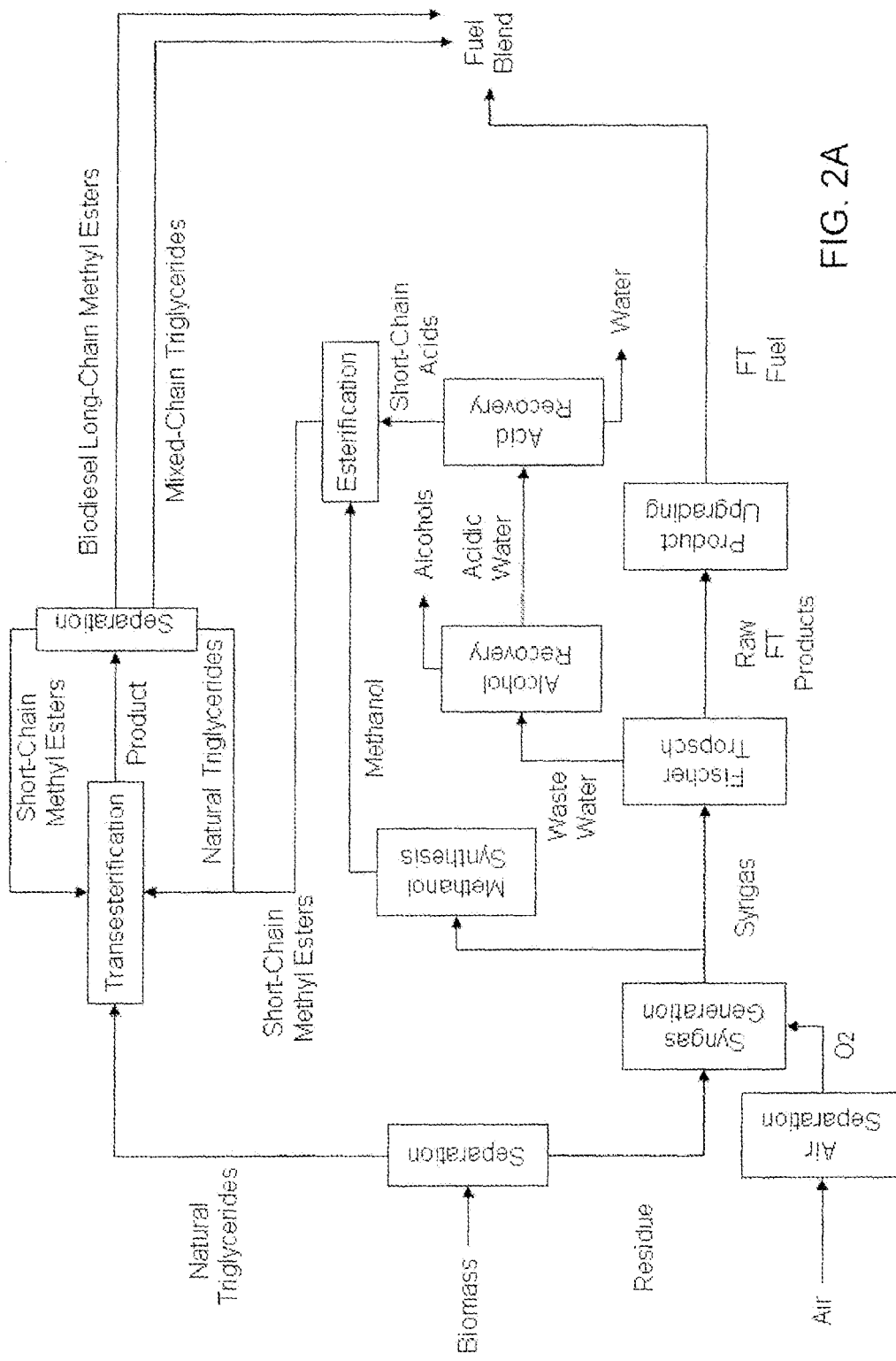
FIG. 2 depicts another embodiment of the process for making a fuel composition of the present invention.
Figure 2B:
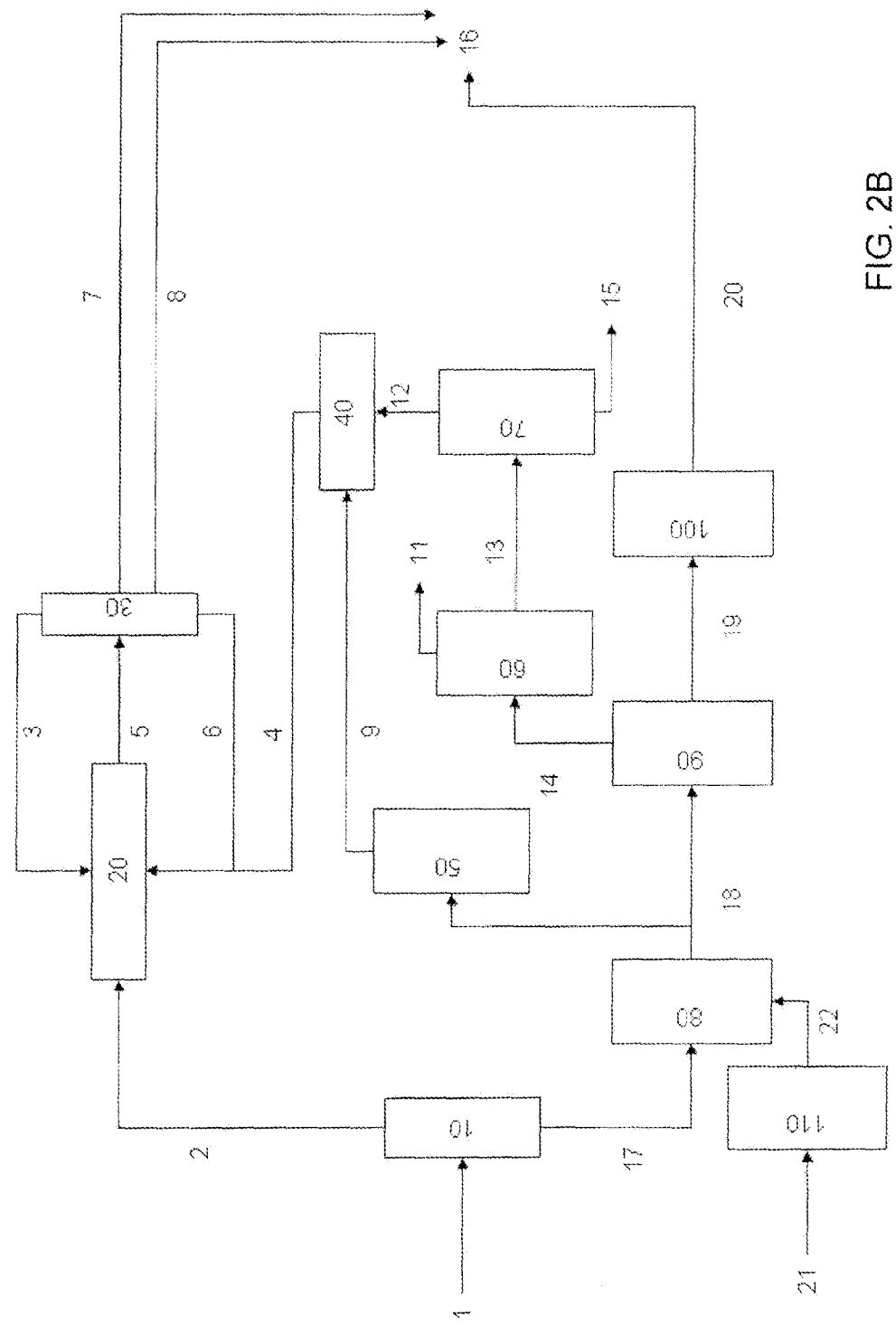

Another embodiment of the process of the present invention is demonstrated in FIG. 2. In this embodiment one variation of the second natural triglyceride process is illustrated. In this embodiment in FIG. 2, an ester is used to transesterify the natural triglycerides, the acids are recovered from the Fischer-Tropsch by-product water, and the methanol is made from a portion of the synthesis gas used in the Fischer-Tropsch process.

Biomass 1 is separated in a separation unit 10 into natural triglycerides 2 and residue 17. The natural triglycerides 2 are transesterified with fresh short-chain methylester 4 and with recycle of unreacted short chain methylester 3 and recycle of unreacted natural triglyceride 6 to form a product 5 which is separated in a separator (such as a distillation unit 30) into the recycle unreacted short chain methylester 3, recycle unreacted natural triglyceride 6, a long-chain methyl ester 7, and mixed-chain triglycerides 8. The biodiesel long-chain methyl ester 7 and the mixed-chain triglycerides 8 are used in a blend to form a fuel blend 16. The residue 17 is gasified in a syngas generation unit 80 by reaction with oxygen 22 that is made in an air separation unit 110 from air 21. The syngas product 18 is separated into two portions. One portion is processed in a Fischer-Tropsch reactor 90 to form a raw Fischer-Tropsch product 19. This raw product is upgraded in a hydrocracker 100 to form a Fischer-Tropsch diesel fuel 20. The Fischer-Tropsch diesel fuel 20 is blended into the fuel blend 16. Another portion of the synthesis gas from the syngas generation unit is reacted in a methanol synthesis unit 50 to make methanol 9. The Fischer-Tropsch reactor 90 also makes a waste water stream 14 which is processed in an alcohol recovery unit 60 to form alcohols 11 and an acidic water 13. The acidic water 13 is processed in an acid recovery unit 70 to form water 15 and short-chain acids 12. The short-chain acids 12 contain acetic acid and high carbon number acids. The recovered acids and the methanol are processed in an esterification unit 40 to make the short-chain methyl esters 4.

Illustrative embodiments of the invention are described above. In the interest of clarity, not all features of an actual embodiment are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover it will be appreciated that such a development effort might be complex and time-consuming, but would nevertheless be a routine undertaking for those of ordinary skill in the art having the benefit of this disclosure.

What is claimed is:

1. A process for manufacturing a low melting point triglyceride of (A) the following formula when there is saturation:

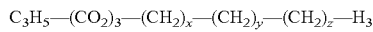

where the values of x, y, and z are not all the same, and the values of x, y, and z are greater than or equal to 0 and up to 19;

and (B) the following formula when there is no saturation:

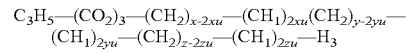

where the values of x, y, and z are not all the same, and the values of x, y, and z are whole positive numbers that are greater than or equal to 0 and less than or equal to 19, and the values of xu, yu and zu are whole positive numbers greater than or equal to 0 and less than or equal to 6, where the values of x, y, z, xu, yu, and zu satisfy the relationship that 2xu is less than or equal to x, 2yu is less than or equal to y, and 2zu is less than or equal to z, the process comprising:

transesterification of a natural triglyceride with an alcohol to form a biodiesel and a glycerol by-product, wherein the alcohol is obtained from the group consisting of purchase, manufacture from synthesis gas used in or as a by-product of a Fischer-Tropsch process, recovery from the waste water from a Fischer-Tropsch process, and combinations thereof, and reacting the glycerol by-product with a short chain acid wherein the acid is obtained from sources selected from the group consisting of recovery from a Fischer-Tropsch process, made by oxidation of Fischer Tropsch alcohols, made by the OXO process using Fischer-Tropsch olefins, made by carbonylation of Fischer-Tropsch alcohols, made by carbonylation of Fischer-Tropsch olefins, and combinations thereof.

2. A process for manufacturing a low melting point triglyceride of (A) the following formula when there is saturation:

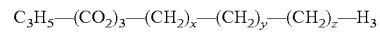

where the values of x, y, and z are not all the same, and the values of x, y, and z are greater than or equal to 0 and up to 19;

and (B) the following formula when there is no saturation:

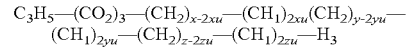

where the values of x, y, and z are not all the same, and the values of x, y, and z are whole positive numbers that are greater than or equal to 0 and less than or equal to 19, and the values of xu, yu and zu are whole positive numbers greater than or equal to 0 and less than or equal to 6, where the values of x, y, z, xu, yu, and zu satisfy the relationship that 2xu is less than or equal to x, 2yu is less than or equal to y, and 2zu is less than or equal to z, the process comprising:

transesterification of a natural triglyceride with an ester to form a biodiesel and a glycerol by-product, wherein the ester comprising an alcohol and an acid, and wherein the alcohol is obtained from the group consisting of purchase, manufacture from synthesis gas used in or as a by-product of a Fischer-Tropsch process, recovery from the waste water from a Fischer-Tropsch process and combinations thereof and wherein the acid is obtained from sources selected from the group consisting of recovery from the waste water from a Fischer-Tropsch process, made by oxidation of Fischer-Tropsch alcohols, made by the OXO process using Fischer-Tropsch olefins, made by carbonylation of Fischer-Tropsch olefins, and combinations thereof.

* * * * *